United States Patent [19]

Schuck et al.

[11] 4,075,197

[45] Feb. 21, 1978

[54] SERUM ALBUMIN PRODUCTION

[75] Inventors: James M. Schuck, Chesterfield; Charles Lewis, Jr., Hazelwood, both of Mo.

[73] Assignee: Monsanto Company, St. Louis, Mo.

[21] Appl. No.: 724,438

[22] Filed: Sept. 20, 1976

[51] Int. Cl.$^2$ .............................................. C07G 7/00
[52] U.S. Cl. ............................... 260/122; 260/112 B; 424/101; 424/177
[58] Field of Search ........................... 260/112 B, 122; 424/101, 177

[56] References Cited

U.S. PATENT DOCUMENTS

| | | | |
|---|---|---|---|
| 2,705,230 | 3/1955 | Reid ...................................... | 260/122 |
| 2,765,299 | 10/1956 | Porsche et al. ...................... | 260/122 |
| 2,958,628 | 11/1960 | Hink .................................... | 260/112 X |
| 3,100,737 | 8/1963 | Auerswald et al. ............. | 260/112 X |
| 3,555,001 | 1/1971 | Wallis et al. ........................ | 260/112 |
| 3,869,436 | 3/1975 | Falksveden ......................... | 260/112 |
| 3,926,939 | 12/1975 | Ivanov et al. ........................ | 260/112 |
| 3,992,367 | 11/1976 | Plan et al. ............................ | 260/112 |

FOREIGN PATENT DOCUMENTS 832,527  12/1975  Belgium.

OTHER PUBLICATIONS

Experientia, vol. 30, No. 6, pp. 608–610, 1974, Podhradska et al.
Blut. Band 30, pp. 121–134, 1975, Schneider et al.

*Primary Examiner*—Howard E. Schain
*Attorney, Agent, or Firm*—Scott J. Meyer; John D. Upham

[57] ABSTRACT

A serum albumin fraction is prepared in high yield and purity from plasma and other albumin-containing blood protein fractions by contacting with a resinous polymeric material having a high capacity for adsorption of albumin, heating at 65°–72° C for about 1–4 hours while maintaining a pH of 5.0–5.5, and then selectively eluting the albumin from the resin-protein mixture at a pH of 3.5–4.5. The resinous polymeric materials are diloweralkylaminoloweralkyl-substituted cross-linked dextran polymers.

13 Claims, No Drawings

SERUM ALBUMIN PRODUCTION

BACKGROUND OF THE INVENTION

This invention relates to blood fractions and more particularly to a method for the preparation of a serum albumin fraction in high yield and purity.

Albumin constitutes the largest fraction of blood plasma and finds wide use in medical therapy such as in cases of shock and as a plasma extender.

The fractionation of blood by various procedures to obtain albumin and recover other separated components is an established practice. A principal albumin fraction of commerce known as normal serum albumin is an osmotically stable solution of a highly purified plasma fraction containing at least 96% albumin. Its availability has been made possible largely through the work of Cohn and his associates at the Harvard Medical School and its preparation is described in U.S. Pat. Nos. 2,390,074 and 2,469,193; *J. Amer. Chem. Soc.* 68, 469–75 (1946); Kirk-Othmer, *Encyl. of Chem. Tech.*, 3, 584–88 (2d. ed. 1964). The current method of choice in the United States for the preparation of normal serum albumin is the so-called Method 6 of Cohn.

Another principal albumin fraction of commerce is the so-called plasma protein fraction (PPF) which is a solution of a plasma fraction containing at least 83% albumin together with a mixture of not more than 17% $\alpha$- and $\beta$- globulins. The current method of choice in the United States for the production of PPF is that of Hink as described in U.S. Pat. No. 2,958,628 and *Vox Sang.* 2, 174 (1957).

The foregoing procedures for obtaining the more highly concentrated normal serum albumin and the less concentrated PPF make use of cold ethanol as a precipitating agent in the fractionation schemes. Various other known procedures for the preparation of albumin fractions make use of other precipitating agents such as ether, methanol or ammonium sulfate salt, or involve adsorption on gels or ion exchange chromatography.

More recently, various polymeric materials have been developed for the fractionation of blood, including the separation of albumin, for example, polyethylene glycol (PEG, Carbowax) as described in U.S. Pat. No. 3,415,804; copolymers of ethylene oxide and polyoxypropylene polymer (Pluronics) as disclosed in U.S. Pat. No. 3,850,903 and German Offenlegunsschrift 2,403,065; and certain unique polyelectrolytes such as ethylene/maleic anhydride, cross-linked copolymer derivatives defined in U.S. Pat. Nos. 3,554,985 and 3,555,001. An advantage of the use of these polymeric materials is that they can be employed at normal room temperature and thus avoid the cold temperature requirements of the Cohn ethanol fractionation procedure.

Still another method of obtaining a purified serum albumin involves the selective denaturation of serum globulins without denaturation of the serum albumin by heating in the presence of caprylate or other fatty acid anion stabilizers as described in U.S. Pat. Nos. 2,705,230 and 2,765,299; *J. Biol. Chem.* 162, 181–98 (1946); and *Blut* 30, 121–134 (1975). While useful for the preparation of PPF type albumin fractions, this method is not generally suitable for the preparation of highly purified serum albumin in high yield without destruction of valuable gamma globulins. It is usually carried out as a pasteurization step to provide a virus-free albumin product.

BRIEF SUMMARY OF THE INVENTION

In accordance with the present invention a serum albumin fraction is prepared in high yield and purity from plasma and other albumin-containing blood fractions by contacting with a resinous polymeric material having high capacity for adsorption of albumin, heating at a temperature of from about 65° to about 72° C for about one to about 4 hours while maintaining a pH of from about 5.0 to about 5.5, and then selectively eluting the albumin from the resin-protein mass at a pH of from about 3.5 to about 4.5. The resinous polymeric materials employed in this invention are diloweralkylaminoloweralkyl-substituted cross-linked dextran polymers. The combination of the heat treatment and the adsorption-elution steps with these dextran polymeric materials provides an albumin product in substantially higher purity and yield than obtained separately with either the heat treatment step or the adsorption-elution steps. Albumin is recoverable in greater than 90% yield and 94% purity by the method of this invention.

DETAILED DESCRIPTION OF THE INVENTION

The serum albumin prepared in accordance with this invention can be obtained from whole blood, blood plasma and serum, or fractions thereof known to contain albumin. Since the treatment with heat as employed herein tends to denature the globulins present in the treated material, it is frequently useful to first isolate certain desired globulin fractions, such as the gamma globulins, before proceeding with the method of the invention. Other valuable blood fractions such as the clotting factors, AHF and prothrombin complex, also can be initially separated from the plasma starting materials before proceeding with the method of the invention. These fractions can be separated by conventional procedures known in the art.

The diloweralkylaminoloweralkyl-substituted cross-linked dextran polymers employed in this invention are described in U.S. Pat. No. 3,227,025, the disclosure of said patent being incorporated herein by reference. These materials are prepared by introducing a suitable diloweralkylaminoloweralkyl functional group such as, for example, the diethylaminoethyl (DEAE) functional group into the cross-linked dextran. By the term loweralkyl is meant an alkyl group having from one to about four carbon atoms.

The cross-linked dextran, available commercially as Sephadex, is a hydrophilic high molecular weight copolymerization product obtained by reacting dextran substances with bifunctional organic substances capable of reacting with the hydroxyl group of said dextran substances as described in U.S. Pat. No. 3,042,667. The cross-linking of the dextran chain gives a 3-dimensional polysaccharide network to which the DEAE or other such functional group is attached by either linkages to the glucose units of the dextran chain. The DEAE cross-linked dextran is available commercially as DEAE-Sephadex A-25 and A-50. The A-25 is more highly cross-linked than the A-50 and has, therefore, a lower porosity. These materials have been used heretofore in the chromatographic separation of albumin from human blood serum, *Experientia* 30 (6), 608–10 (1974); and in the production of other blood proteins such as the immunne globulins as described in *Arch. Biochem. Biophys.* 108, 514–22 (1964), 134, 279–84 (1969); *Vox Sang.* 23 (4), 279–90 (1972), and U.S. Pat. No. 3,869,436;

and prothrombin as disclosed in *Vox Sang.* 25 (2), 113–23 (1973) and U.S. Pat. No. 3,920,625.

In a recent Belgian patent 832,527, DEAE-dextran is disclosed as useful in the preparation of a very pure albumin fraction. In the described method, blood plasma is contacted with the resin, followed by elution and then heat treatment of the eluant solution in the presence of acetyl tryptophan or medium chain length fatty acids. While the procedure is useful, it does not have the advantage of separating the denatured globulins from the albumin which is facilitated by heat treatment of the resin-protein mixture in accordance with the present invention.

In carrying out the method of this invention, the foregoing resinous dextran polymeric material is admixed with blood plasma or serum, or albumin-containing blood fractions, preferably at a concentration ranging from about 1% to about 5% polymer. By adjusting the pH of the resin-protein mixture to varying levels, selected proteins can first be removed. At pH of about 5.5 to 7.5, albumin, $\alpha$ and $\beta$ globulins and fibrinogen are adsorbed by the resin while a major portion of the gamma-globulin remains unadsorbed and can be recovered from the supernatent for therapeutic use. Preferably, this initial separation of gamma globulin is carried out at a pH of about 6. A portion of the adsorbed $\alpha$- and $\beta$-globulins and fibrinogen can then be recovered by adjusting the resin-protein mixture to a pH of about 4.7 and collecting the desorbed supernatent.

The resin-protein mixture can then be adjusted to a pH range of from about 5.0 to about 5.5 and heated at a temperature of from about 65° C to about 72° C for about one to about four hours. Preferably, the pH is adjusted to about 5.2–5.3 and the resin-protein mixture is heated at about 70° C for about one hour.

During the heat treatment step, the residual globulins, principally the $\alpha$- and $\beta$-globulins, are denatured while at the same time the albumin is not denatured and is readily recoverable.

Following the heat treatment, the pH is adjusted to a range of from about 3.5 to about 4.5 to elute the desired albumin from the resin-protein mixture. Preferably, the resin-protein mixture is cooled prior to the pH adjustment and the pH is then adjusted to about 4.

The recovery of the albumin can be carried out by a variety of separation techniques such as sedimentation, filtration, or centrifugation, but preferably by filtration of the pH-adjusted resin-protein mixture, washing of the filter cake and collection of the filtrate as the desired highly purified albumin fraction.

Adjustment of the pH to the desired level during the foregoing processing can be carried out by treatment with acid or alkaline buffer materials known to be clinically acceptable, for example, by the use of sodium acetate-acetic acid buffer or citric acid for acdification or by the use of sodium bicarbonate or sodium hydroxide to increase alkalinity.

It is also preferable to include known albumin stabilizers such as sodium acetyl tryptophanate and sodium caprylate in the resin-protein mixture during the heat treatment step for their known stabilizing properties.

The following examples will further illustrate the invention although it will be appreciated that the invention is not limited to these specific examples.

EXAMPLE 1

In this example, the resinous polymeric material consisted of DEAE-Sephadex A-50 which is a commerically available diethylaminoethyl-substituted cross-linked dextran polymer. Initially, the polymeric resin was washed in 0.04 molar NaCl. Plasma obtained from pooled human blood was diluted with three parts of water to one part of plasma and then admixed with 2% by weight of the washed resin (2G/100 ml). The resin-plasma mixture was adjusted to a pH of 6.0, mixed for 30 minutes, filtered and then washed with 0.002 molar NaCl. The filtrate, which consisted of predominantly gamma globulins, beta globulins, fibrinogen and associated blood factors, was separated from the remaining resin-protein filter cake. The resin-protein filter cake, which contained the adsorbed albumin, was acidified to a pH of 5.2. Sufficient sodium caprylate stabilizer was admixed with the resin-adsorbed protein to provide a 0.012 molar concentration and NaCl was added to give a 0.002 molar concentration. Heating of the resin-adsorbed protein was then carried out at 70° C for one hour. The suspension was cooled to room temperature, after which time the material was filtered and the filtrate was discarded. The albumin was eluted from the remaining resin-protein filter cake by acidifying to pH 4.0 in 0.002 molar NaCl with citric acid, mixing for 30 minutes, and filtering. The filtrate was retained as the desired albumin fraction in a yield of 91:5% (basis: concentration of albumin in original plasma) and a purity of 95.2%. Albumin purity of the product eluted from the resin was determined by agarose gel electrophoresis in barbital buffer at pH 8.6 with a Corning ACI electrophoresis apparatus. In this determination, a Coomassie Brilliant Blue R 250 (C.I. 42660) staining procedure was used substantially in accordance with the procedure described by Fazekas de St. Groth et al, *Biochim. Biophys. Acta* 71, 377–91 (1963), and the readings were made with a Gelman ACD-15 densitometer at 600 nm. Coomassie Brilliant Blue R 250 is a protein stain of great sensitivity which follows Beer's law up to 20 ug/cm of width and is sensitive down to 0.5 ug/cm of width. As a result of this sensitivity, Coomassie Brilliant Blue R 250 enables the detection of protein contaminants in the albumin product to a high degree and the stated assay confirms the preparation of an albumin product of high purity.

EXAMPLE 2

The procedure of Example 1 is repeated except that the starting plasma is an AHF-depleted plasma. The yield and purity of the albumin product are substantially similar to that obtained in Example 1.

EXAMPLE 3

The procedure of Example 1 is repeated except that an intermediate step is carried out after the first filtration prior to the heat treatment step in order to remove additional globulins and fibrinogen from the plasma. In this intermediate step, the resin-protein filter cake from the first filtration is adjusted to pH 4.7 in 0.002 molar NaCl with citric acid and mixed for 30 minutes. The mixture is filtered, washed and then subjected to the heat treatment and subsequent steps of Example 1. The filtrate from the treatment at pH 4.7 contains alpha and beta globulins and fibrinogen which can be retained for various known therapeutic or diagnostic uses. The final albumin product is obtained in a yield and purity substantially similar to that of Example 1.

Following the recovery of the purified albumin product in accordance with this invention, the albumin can be concentrated to a desired level and the concentrated product can be adjusted to a physiologically acceptable pH and electrolyte content, further heated to destroy virus, and clarified by filtration or other such procedures to provide a clinically acceptable product. Examples of useful concentration procedures which can be used are (1) lyophilization followed by redissolution to a desired level such as 5% or 25%, and (2) ultrafiltration.

Various other examples will be apparent to the person skilled in the art after reading the foregoing specification without departing from the spirit and scope of the invention and it is intended that all such examples be included within the scope of the appended claims.

What is claimed is:

1. A method for the production of a serum albumin fraction in high yield and purity from admixture with other blood protein components comprising contacting the albumin-protein mixture with a resinous polymeric material selected from the group consisting of dilowerlalkylaminoloweralkyl-substituted cross-linked dextran polymers, heating at a temperature of from about 65° C to about 72° C and at a pH of from about 5.0 to about 5.5 for about one to about four hours and then adjusting the mixture to a pH of from about 3.5 to about 4.5 to selectively elute the desired albumin therefrom.

2. The method of claim 1 in which the resinous polymeric material is used in a concentration of from about 1% to about 5% by weight of the albumin-protein mixture.

3. The method of claim 1 in which the pH during the heat treatment step is from about 5.2 to about 5.3.

4. The method of claim 1 in which the pH during the elution step is about 4.0.

5. The method of claim 1 in which the heat treatment is carried out at a temperature of about 70° C.

6. The method of claim 1 in which the albumin-protein mixture is whole blood plasma.

7. The method of claim 1 in which the albumin-protein mixture is an AHF-depleted blood plasma fraction.

8. The method of claim 1 in which the diloweralkylaminoloweralky is diethylaminoethyl.

9. The method of claim 1 in which the albumin-protein mixture is blood plasma which has been fractionated initially to remove gamma globulin.

10. The method of claim 9 in which the initial fractionation to remove gamma globulin comprises contacting the albumin-protein mixture with the resinous polymeric material at a pH of from about 5.5 to about 7.5 and separating the unadsorbed material therefrom as the gamma globulin fraction.

11. The method of claim 10 in which the diloweralkylaminoloweralkyl is diethylaminoethyl.

12. The method of claim 10 in which the initial fractionation is carried out at a pH of about 6.0.

13. The method of claim 9 including the additional step of removing alpha and beta globulins comprising adjusting the resin-adsorbed albumin-protein mixture to a pH of about 4.7 and separating the desorbed supernatant therefrom.

* * * * *